United States Patent [19]

Schlain et al.

[11] Patent Number: 5,271,398

[45] Date of Patent: Dec. 21, 1993

[54] INTRA-VESSEL MEASUREMENT OF BLOOD PARAMETERS

[75] Inventors: Leslie A. Schlain; Philip G. Ralston, both of The Woodlands, Tex.

[73] Assignee: Optex Biomedical, Inc., The Woodlands, Tex.

[21] Appl. No.: 774,693

[22] Filed: Oct. 9, 1991

[51] Int. Cl.[5] ............................... A61B 5/00
[52] U.S. Cl. ........................... 128/634; 128/632; 128/637
[58] Field of Search ............... 128/637, 634, 633, 632

[56] References Cited

U.S. PATENT DOCUMENTS

| | | |
|---|---|---|
| 3,068,742 | 12/1962 | Hicks, Jr. et al. . |
| 3,123,066 | 3/1964 | Brumley . |
| 3,529,591 | 9/1970 | Schuette ........................ 128/2.05 |
| 4,474,183 | 10/1984 | Yano et al. . |
| 4,478,222 | 10/1984 | Koning et al. ..................... 128/632 |
| 4,682,895 | 7/1987 | Costello ........................ 128/636 |
| 4,752,115 | 6/1988 | Murray, Jr. et al. . |
| 4,758,298 | 7/1988 | Goorsky et al. ..................... 156/296 |
| 4,785,823 | 11/1988 | Eggers et al. ..................... 128/692 |
| 4,813,423 | 3/1989 | Miyasaka et al. ..................... 128/692 |
| 4,830,013 | 5/1989 | Maxwell ........................ 128/637 |
| 4,934,369 | 6/1990 | Maxwell ........................ 128/637 |
| 4,951,669 | 8/1990 | Maxwell et al. ..................... 128/637 |
| 4,991,590 | 2/1991 | Shi . |
| 5,012,809 | 5/1991 | Shulze . |
| 5,054,882 | 10/1991 | Riccitelli et al. . |
| 5,174,299 | 12/1992 | Nelson ........................ 128/692 |
| 5,195,963 | 3/1993 | Yafuso et al. ..................... 604/49 |

FOREIGN PATENT DOCUMENTS

| | | |
|---|---|---|
| 82303162.1 | 6/1982 | European Pat. Off. . |
| 84303207.9 | 5/1984 | European Pat. Off. . |
| 89113197.1 | 7/1989 | European Pat. Off. . |
| 56-124036 | 9/1981 | Japan . |

OTHER PUBLICATIONS

Pending Application U.S. Serial No. 07/526,822 filed May 22, 1990.
"Progress in the Development of a Fluorescent Intravascular Blood Gas System in Man", Mahutte et al., 1989.
"Fiberoptic Sensors Evolve Into Medical Products", Moretti, Laser Focus/Electro Optics, May, 1987.
"Continuous Measurement of Intraarterial pHa, PaCO2, and PaO2 in the Operating Room," Barker et al., 1991.
"Critical Care Perspectives-Controversies and Pitfalls in Arterial Blood Gas Monitoring" Franklin, 1990; Dellinger, 1990.

*Primary Examiner*—Randall L. Green
*Assistant Examiner*—Gina M. Gualtieri
*Attorney, Agent, or Firm*—Guy McClung

[57] ABSTRACT

Methods and apparatuses for detecting undesirable wall effect on blood parameter sensors and for moving such sensors to reduce or eliminate said wall effect; and, in one aspect, a sensor with a plurality of spaced apart sensing elements with respect to which wall effect is reduced upon rotation of the sensor.

8 Claims, 3 Drawing Sheets

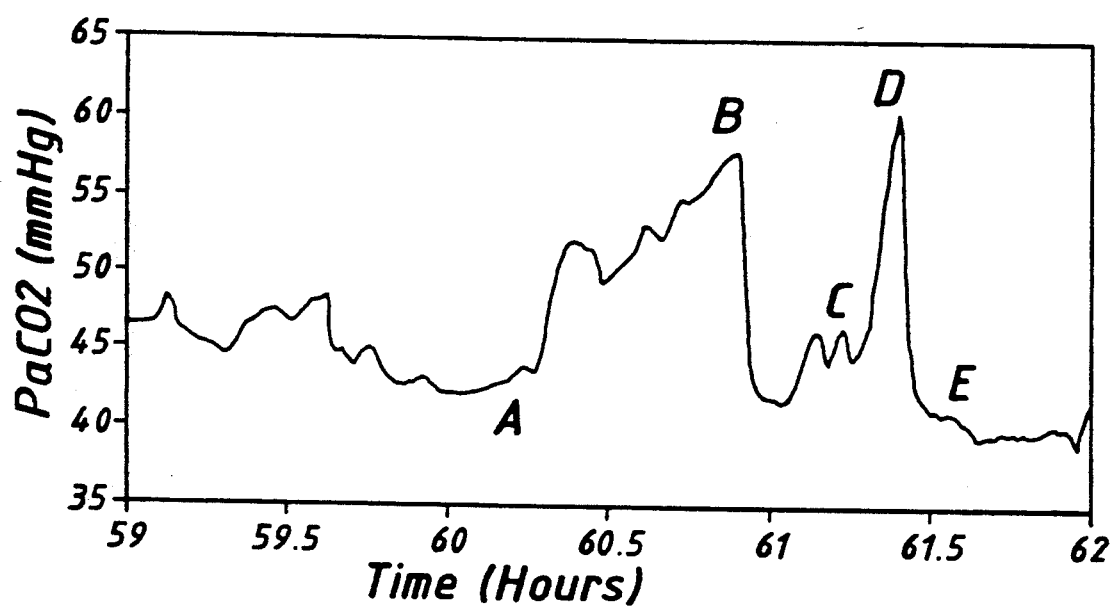

INTRA-VESSEL MEASUREMENT OF BLOOD PARAMETERS

BACKGROUND OF THE INVENTION

1. Field of the Invention

This invention is in the field of measurement of the various constituents of blood and, in one particular aspect, is related to the intra-corporeal measurement of the concentration of various blood constituents.

2. Description of Related Art

The prior art discloses a variety of sensors, probes and instruments used intra-corporeally for measuring blood parameters.

U.S. Pat. No. 4,682,895 to Costello discloses a fiber optic probe with a side sample chamber for intracorporeal insertion into blood vessels to measure various blood parameters. The side sample chamber includes a gap between two ends of a fiber optic and, necessarily, this side sample chamber assumes some singular disposition within a blood vessel.

Pending U.S. application Ser. No. 07/526,822 filed on May 22, 1990 by Costello et al. discloses a multi-sensor optical fiber probe for intra-corporeal insertion into blood vessels to measure various blood parameters. The probe may have a plurality of side sample chambers disposed at various positions about the circumference of the probe. In using the probe, one or more of the side sample chambers may be disposed near, directly adjacent, or in contact with a portion of the interior wall surface of a blood vessel.

U.S. Pat. No. 4,758,298 discloses a multi-sensor probe in which a plurality of fiber optics are bonded to each other. Sensing elements on each separate sensor are staggered in relation to each other. Each individual sensor is constructed with the sensing element between ends of optical fibers. In using the probe one or more of the sensing elements may be positioned near, directly adjacent, or in contact with a portion of the interior wall surface of an arterial cannula or blood vessel.

U.S. Pat. No. 4,830,013 discloses an in vivo blood parameter probe measurement system with one or more sensors at a distal end thereof. The probe is centrally moved back and forth in a catheter from a space filled with saline solution to a space filled with blood. One stated reason for keeping the probe centered within the catheter is to avoid the detrimental aspects of "wall effect." Wall effect occurs when a blood sensor's sensing element or area comes into contact with or in close proximity to a portion of the side wall of a blood vessel. Active metabolism of the cells of the blood vessel wall and/or the effects of restricted blood flow between the sensor(s) and the blood vessel wall can result in a microenvironment which is unlike that of the area of less restricted blood flow thus producing inaccurate measurements of the various blood parameters. Also, a probe may contact and sense wall tissue instead of blood. The method disclosed in U.S. Pat. No. 4,830,013 can result in erroneous results due to the undesirable mixing of infused saline solution and the blood being measured.

"Progress in the Development of a Fluorescent Intravascular Blood Gas System in Man," by Mahutte et al., 1989, discusses the deleterious effects of wall effect caused by a sensor touching a blood vessel wall and hence indicating a reading based in part on the nature of the tissue with which the sensor is in contact. A probe with three $PO_2$ sensors distributed axially with two sensors located at different positions back from the probe tip was rotated 180 degrees to move one sensor away from the wall, but another sensor was then adversely affected by the wall effect. This reference teaches that a probe tip had to be retracted within an intra-arterial cannula tip to reduce the wall effect.

There is a need for a solution to the problem of blood parameter sensor disposition to avoid the detrimental effects of "wall effect." There is a need for a blood parameter sensor which produces accurate measurements from within the blood vessel without the need for maintaining the sensor within a artificial member such as a catheter.

Any unnecessary addition of instruments or structure into an area of blood flow is associated with the possibility of the production of undesirable thrombogenesis or clot formation. There is a need for methods and apparatuses for blood parameter sensing and measurement with which the level of thrombogenesis is reduced.

SUMMARY OF THE PRESENT INVENTION

The present invention teaches methods and apparatuses for reducing "wall effect" in intra-vessel sensing of blood parameters. These methods and apparatuses are useful in any conduit through which blood flows including both extra-corporeal conduits such as flow tubing and intra-corporeal blood vessels such as veins and arteries. In one aspect the present invention discloses a method in which a system has a sensor, apparatus for detecting sensor position, and apparatus for moving the sensor if detrimental results of wall effect are detected, e.g., but not limited to, declining oxygen concentration or increasing carbon dioxide concentration.

Continuous monitoring of the sensor(s) indicates both the incidence of detrimental wall effect and then a leveling off of a particular parameter establishing that the sensor has been moved so that acceptable readings are being obtained.

In one embodiment the present invention teaches a method for detecting the influence of wall effect on a blood parameter sensor disposed in a blood flow conduit, the method including detecting and measuring the blood parameter, compiling a plurality of measurements of the blood parameter over a time period, and comparing the measurements to determine whether the level of the blood parameter is changing indicating that the measurement is influenced by wall effect. Another embodiment of the present invention discloses a method for changing the disposition of a blood parameter sensor in a blood flow conduit to reduce or eliminate wall effect on measurements of the blood parameter, the method including detecting and measuring the blood parameter and moving the blood parameter sensor so that the wall effect is reduced permitting accurate measurement of the blood parameter.

Another embodiment of the present invention teaches a multi-sensor blood parameter measurement probe that has a body member of length suitable for insertion into a blood flow conduit (such as, but not limited to, an artery in vivo e.g. to a length just outside of an arterial cannula to a distance of up to two inches or more from the end of the cannula, i.e. to a portion of the artery which has not constricted or to a portion which is larger than the point at which the cannula enters the artery), the conduit having an interior wall surface, and the body member having therein or thereon two or more spaced apart blood parameter sensing elements, the sensing elements disposed in relationship to each other so that rotational movement of the body member about a longitudinal axis thereof reduces wall effect of the conduits interior wall surface on the two or more sensing elements.

It is, therefore, an object of the present invention to provide new, useful, unique, efficient, and effective devices and methods for measuring blood parameters.

Another object of the present invention is the provision of such devices and methods useful within the blood vessels in vivo.

Yet another object of the present invention is the provision of such methods and devices which reduce or overcome detrimental wall effect within blood vessels or other conduits.

An additional object of the present invention is to provide such methods and devices for moving a sensor or sensors so that wall effect is reduced or avoided.

Another object of the present invention is the provision of such devices and methods which provide an indication that an acceptable sensor position has been achieved.

Yet another object of the present invention is the provision of such devices and methods which reduce the need for structures and sensor positions which promote clot formation.

The present invention recognizes and addresses the previously-mentioned long-felt needs and provides a satisfactory meeting of those needs in its various possible embodiments. To one of skill in this art who has the benefits of this invention's teachings and disclosures, other and further objects and advantages will be clear, as well as others inherent therein, from the following description of presently-preferred embodiments, given for the purpose of disclosure, when taken in conjunction with the accompanying drawings. Although these descriptions are detailed to insure adequacy and aid understanding, this is not intended to prejudice that purpose of a patent which is to claim an invention no matter how others may later disguise it by variations in form or additions of further improvements.

DESCRIPTION OF THE DRAWINGS

So that the manner in which the above-recited features, advantages and objects of the invention, as well as others which will become clear, are attained and can be understood in detail, more particular description of the invention briefly summarized above may be had by reference to certain embodiments thereof which are illustrated in the appended drawings, which drawings form a part of this specification. It is to be noted, however, that the appended drawings illustrate preferred embodiments of the invention and are therefore not to be considered limiting of its scope, for the invention may admit to other equally effective equivalent embodiments.

FIG. 4b is a perspective view of the probe of FIG. 4a.

FIG. 5 presents a graph which illustrates the occurrence of wall effect and rotation of a probe to counteract the wall effect.

DESCRIPTION OF EMBODIMENTS PREFERRED AT THE TIME OF FILING FOR THIRD PARENT

Figure 1:
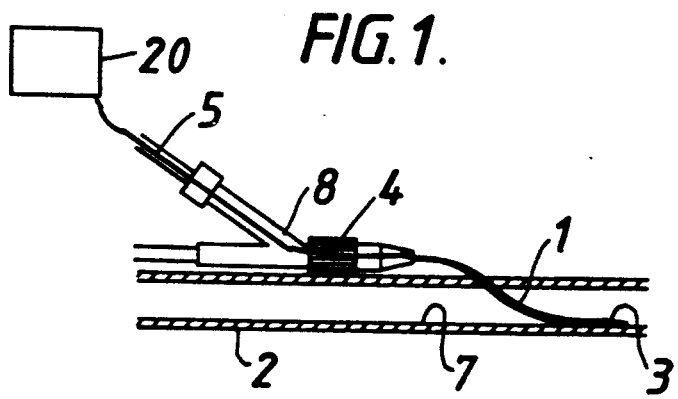
FIG. 1 is a side cross-sectional view of a blood parameter sensor in vivo within a blood vessel.

Referring now to FIG. 1, a cannula 1 is inserted in vivo into a blood vessel 2 which has an interior wall 7. A blood sensor probe 5 is inserted into and through the cannula 1 and into the blood vessel 2 so that a distal end 3 of the probe 5 extends into the blood vessel 2. Sensing areas or elements of the probe (not shown) are originally in a first position with respect to the blood vessel interior wall 7. A threaded connector 4 mates with a threaded body 8 holding the probe 5 in position with respect to the cannula 1, thereby maintaining the position of the probe 5 within the blood vessel 2. Rotation of the body 8 rotates the probe 5 in the blood vessel 2.

A detection apparatus 20 interfaces with the probe 5 and provides an indication of a level of a blood parameter sensed by each of the sensing elements.

Figure 2:
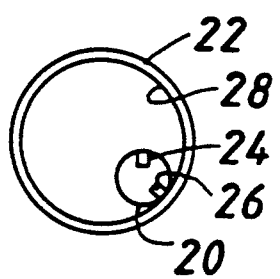
FIG. 2 is an end cross-sectional view of a blood parameter sensor in a blood conduit.

Unusual or anomalous readings may indicate that one or more of the sensing elements (e.g. sensing elements 6 as shown in FIG. 2) are in contact with or relatively near the wall 7 of the blood vessel 2 such that wall effect is responsible for inaccurate measurements. Rotation of the body 8 results in rotation of the distal end 3 of the probe 5 and subsequent readings indicated by the device 20 indicate that the distal end 3 of the probe 5 has been rotated so that the sensing elements 6 are disposed away from the wall 7 for accurate blood parameter measurement.

Figure 3:
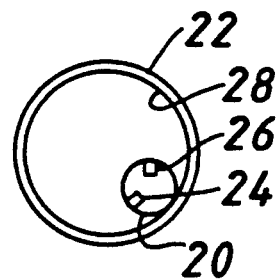
FIG. 3 is an end cross sectional view of the blood parameter sensor of FIG. 2 shown in a different position.

FIG. 2 shows a probe 20 in a blood flow vessel or conduit 22. The probe 20 has blood parameter sensing elements 24 and 26. Sensing element 26 is in contact with an interior wall 28 of the vessel 22 and is, therefore, subject to the undesirable results of wall effect. FIG. 3 shows the probe 20 rotated to a new position in which both sensing elements are well away from the wall 28 so that the wall effect is reduced or eliminated.

Applicants believe that wall effect is demonstrated by a sudden change in the level of blood parameter when there is no change in the condition of a patient in whom a probe is resident. Since normal ranges of $CO_2$, $O_2$, and pH are known for human tissue, a sudden change in an indicated value for a blood parameter, (particularly a change which produces a value reading that more closely approximates the value of that parameter for human tissue) is believed to indicate wall effect, i.e., an undesirable position of a probe in a blood vessel. Also upon compiling several readings over time during a particular procedure of a particular blood parameter, any sudden or dramatic excursion from these values may indicate that a probe has moved near to or against a vessel wall. Usually a sudden unexpected decrease in pH or $O_2$ levels or a sudden unexpected increase in $CO_2$ level indicates wall effect. This is particularly true if a sudden increase occurs in blood $CO_2$ level without a corresponding decrease in blood pH level.

FIG. 5 illustrates an occurrence of wall effect and employment of a method and apparatus according to the present invention to counteract the wall effect. The vertical axis in FIG. 5 indicates $CO_2$ concentration in millimeters of mercury. The horizontal axis indicates time in hours. A multi-sensor probe as disclosed in pending U.S. application Ser. No. 07/526,822 filed on May 22, 1990 was inserted in vivo into a human artery. The sensing elements of this probe included pH, $CO_2$, and $O_2$ sensing elements--and they were disposed generally on one side of the probe within an arc of about 120 degrees when viewed from the end in cross-section (a disposition not shown in the above-identified application). At about 60 hours and 5 minutes into the test, an apparent sudden dramatic increase in measured $CO_2$ occurred, (from point A to point B on the graph) an increase from about 43 mm Hg to about 57 mm Hg. Rotation of the probe 30 degrees to the right immediately brought the $CO_2$ reading down, indicating that the probe had been moved so that the sensing elements were no longer near or in contact with the vessel wall. To check to see if indeed the probe had been subject to wall effect, the operator rotated the probe back 30 degrees to the left to approximate the previous undesirable position (indicated by the change from point C to point D on the graph) and the wall effect was duplicated. Again the probe was rotated 30 degrees to the right (indicated by the change from point D to point E on the graph) to reposition the sensing elements and permit accurate blood gas readings uninfluenced by wall effect.

Figure 4A:
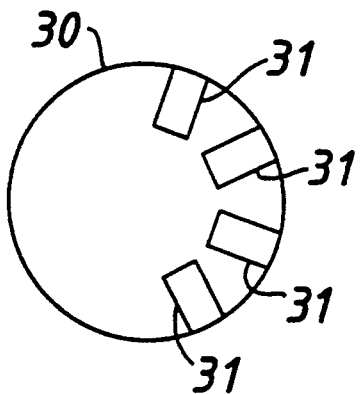
FIG. 4a is an end cross-sectional view of a multisensor probe.
Figure 4B:
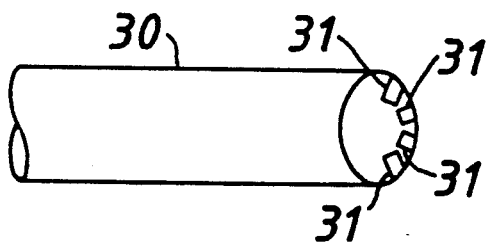

FIG. 4a and 4b show a probe 30 according to the present invention that includes a plurality of spaced apart sensing elements 31 all of which are relatively close together and preferably within an arc of less than 180° [and most preferably within an arc of 120° or less] as viewed from the end of the probe 30. The elements 31 are shown within the probe 30 but it is within the scope of this invention for them to be on rather than within the probe. The sensing elements 3 are shown at a probe end, but it is within the scope of this invention for them to be disposed at any point on the probe so long as their blood sensing function can be accomplished. It is also within the scope of this invention to detect readings from a probe used within a blood flow conduit and, if desirable, to rotate a probe (such as the probe disclosed in U.S. Pat. No. 4,830,013) within a conduit other than an in vivo blood vessel. It is also within the scope of this invention to provide a method which is the alternate of the methods described above; i.e., a method for detecting and measuring parameters of intra-vessel wall tissue by selectively moving a probe from a more central blood measuring position to a position adjacent to or in contact with the wall.

Figure 6A:
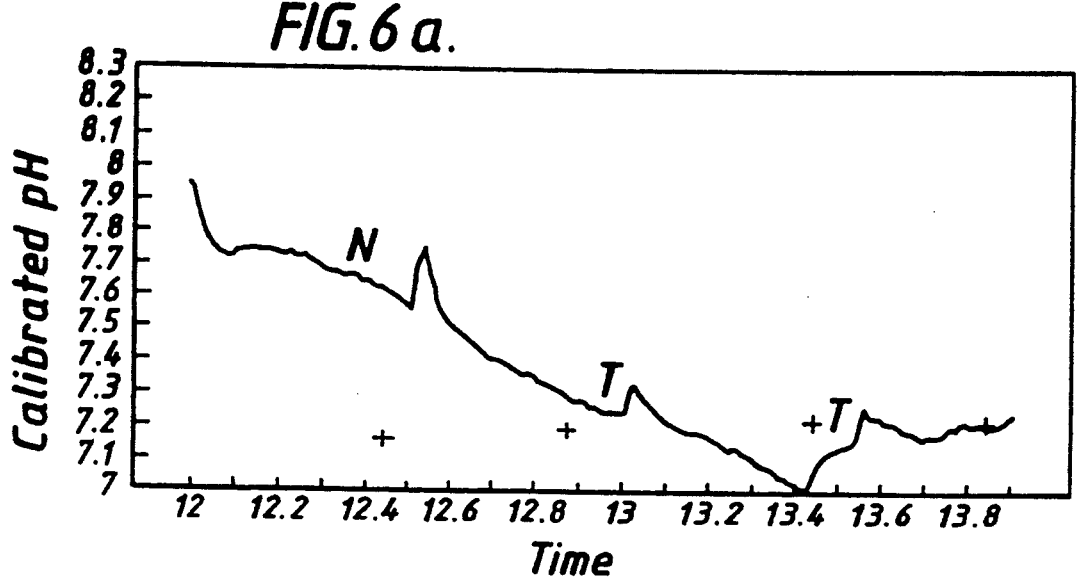
FIG. 6 presents graphs illustrating the occurrence of wall effect and rotation of a probe to counteract it.
Figure 6B:
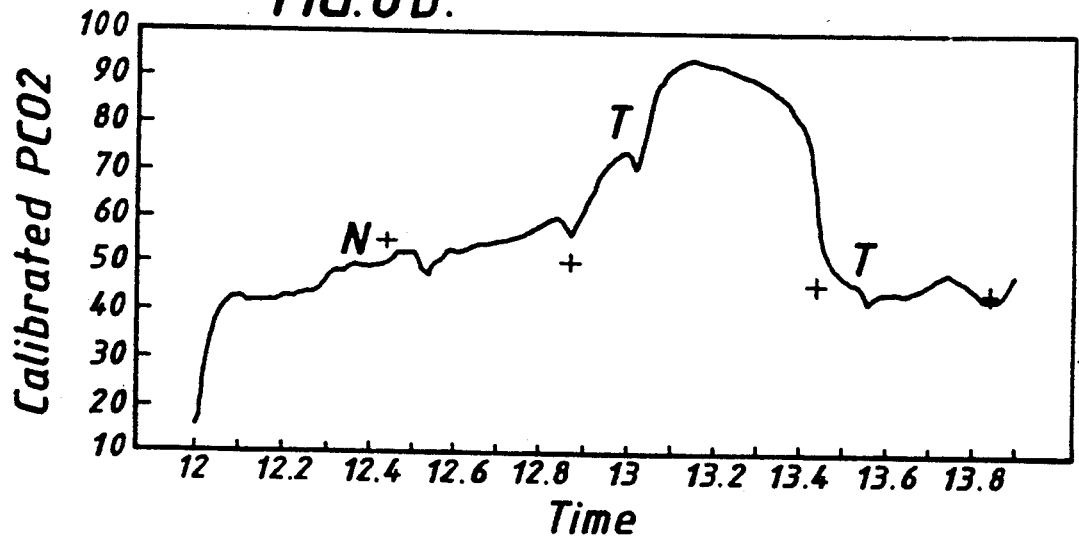
Figure 6C:
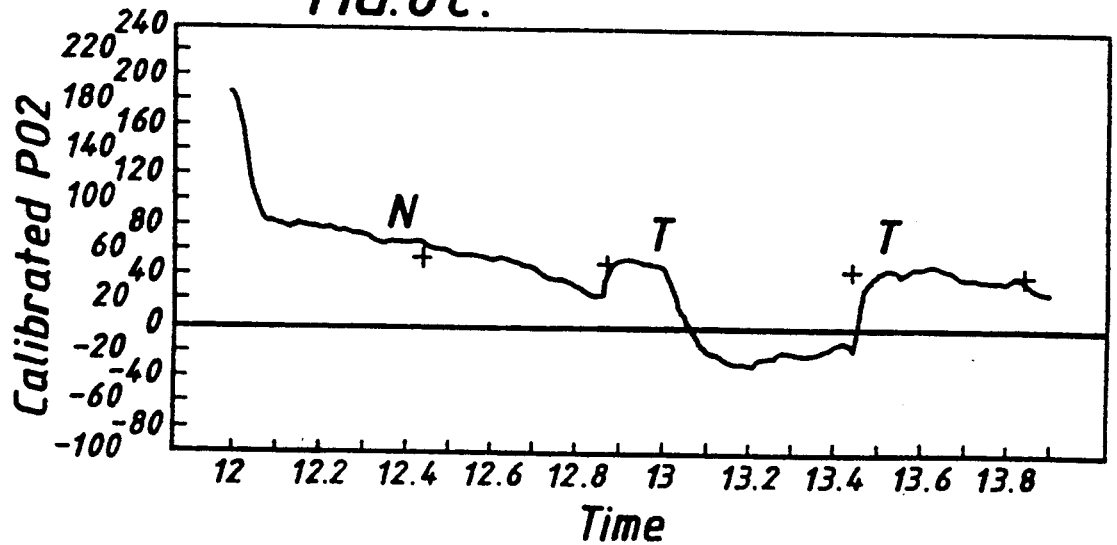

FIG. 6 illustrates the simultaneous wall effect on all the sensing elements of a single multi-sensor probe having sensing elements for indicting $CO_2$ and $O_2$ concentrations and pH level. All three sensing elements were in an arc of less than 180 degrees of the probe cross-section. Between the time as indicated on the horizontal axes of the three graphs as about "13" and about "13.5," there is indicated a decrease in pH, a corresponding increase in $CO_2$ level, and a decrease in $O_2$ level. These changes were due to accidental, unintended rotation of the probe resulting in the probe contacting the wall of the vessel in which it was positioned and the ensuing undesirable wall effect on the probe readings. Rotation of the probe to its original position resulted in re-establishment of a probe position away from the vessel wall (in this case an artery of a dog) and the resumption of normal readings unaffected by wall effect. The vertical axes of the three graphs indicate calibrated values for pH (top graph); $CO_2$ concentration (middle graph); and $O_2$ concentration (lower graph). For more accurate readings there may be cases in which an artery is constricted at one area (e.g. at an area of trauma or an area of cannula entry) and location of a probe at a wider area of an artery is desired. This is accomplished by extending the probe further in the artery (or other vessel or conduit) to an area of larger cross-section.

In conclusion, therefore, it is seen that the present invention and th embodiments disclosed herein are well adapted to carry out the objectives and obtain the ends set forth at the outset. Certain changes can be made in the method and apparatus without departing from the spirit and the scope of this invention. It is realized that changes are possible and it is further intended that each element or step recited in any of the following claims is to be understood as referring to all equivalent elements or steps for accomplishing substantially the same results in substantially the same or equivalent manner. It is intended to cover the invention broadly in whatever form its principles may be utilized. The present invention is, therefore, well adapted to carry out the objects and obtain the ends and advantages mentioned, as well as others inherent therein.

What is claimed is:

1. A method for changing disposition of a blood parameter sensor and for reducing or eliminating the effect of wall effect on the sensor, the sensor having at least one sensing element, the at least one sensing element being located in flowing blood in a blood vessel through which blood flows the method comprising detecting and measuring a blood parameter of the flowing blood with the at least one sensing element, compiling a plurality of measurements of the blood parameter over a time period, comparing the measurements to determine whether the blood parameter is changing, moving the at least one sensing element while maintaining it in the flowing blood with nothing between the at least one sensing element and the wall of the blood vessel other than the flowing blood, and moving the at least one sensing element so that wall effect on the at least one sensing element is reduced permitting more accurate measurement of the blood parameter.

2. The method of claim 1 wherein the at least one sensing element is a plurality of two or more sensing elements.

3. The method of claim 1 wherein moving the at least one sensing element is done by rotating the sensor within the blood vessel.

4. The method of claim 1 wherein the blood vessel is an in vivo intracorporeal blood vessel.

5. The method of claim 1 wherein the at least one sensing element is three sensing elements, including one each for sensing pH, oxygen content and carbon dioxide content of the blood.

6. The method of claim 2 wherein the sensing elements are in an arc of the sensor when viewed from an end thereof of lens than 180 degrees.

7. The method of claim 1 wherein there are three sensing elements and they are in an arc of the probe when viewed from an end thereof of about 120 degrees.

8. The method of claim 1 wherein the sensor has one or more fiber optics in or on which is the at least one sensing element.

* * * * *